United States Patent [19]

Pfister et al.

[11] Patent Number: 5,232,702
[45] Date of Patent: Aug. 3, 1993

[54] SILICONE PRESSURE SENSITIVE ADHESIVE COMPOSITONS FOR TRANSDERMAL DRUG DELIVERY DEVICES AND RELATED MEDICAL DEVICES

[75] Inventors: William R. Pfister, Bay City; Jeniffer M. Wilson, Saginaw, both of Mich.

[73] Assignee: Dow Corning Corporation, Midland, Mich.

[21] Appl. No.: 733,497

[22] Filed: Jul. 22, 1991

[51] Int. Cl.⁵ ............................................. A61F 13/02
[52] U.S. Cl. .................... 424/448; 424/443; 424/449; 525/477; 525/478
[58] Field of Search ............... 424/448, 449, 447, 443; 525/477, 478

[56] References Cited

U.S. PATENT DOCUMENTS

| | | | |
|---|---|---|---|
| 3,528,940 | 9/1970 | Modic | 260/37 |
| 4,719,226 | 1/1988 | Otsuka et al. | 514/449 |
| 4,925,671 | 5/1990 | Abber | 424/448 |
| 4,978,532 | 12/1990 | El-Rashidz | 424/448 |
| 5,035,894 | 7/1991 | Lee et al. | 424/448 |
| 5,045,319 | 9/1991 | Chien et al. | 424/448 |

FOREIGN PATENT DOCUMENTS

0224981A2 7/1986 European Pat. Off. .
WOA9109633 7/1991 PCT Int'l Appl. .

Primary Examiner—Thurman K. Page
Assistant Examiner—Leon R. Horne
Attorney, Agent, or Firm—John L. Chiatalas

[57] ABSTRACT

A silicone pressure sensitive adhesive composition which is compatible with drugs, excipients, co-solvents and skin penetration enhancers is disclosed which includes a cohesive strengthening agent in combination with a silicone fluid and a silicate resin. The addition of the cohesive strengthening agent helps to maintain the adhesive on the substrate, while reducing cold flow. The adhesive is useful as an improved component in transdermal drug delivery devices and related medical devices.

22 Claims, 1 Drawing Sheet

SILICONE PRESSURE SENSITIVE ADHESIVE COMPOSITONS FOR TRANSDERMAL DRUG DELIVERY DEVICES AND RELATED MEDICAL DEVICES

TECHNICAL FIELD

This invention relates to silicone pressure sensitive adhesive compositions having improved cohesive strength and stability, and transdermal-type drug delivery devices and related medical devices for using the compositions.

BACKGROUND OF THE INVENTION

A pressure sensitive adhesive is generally a material which adheres to a surface with slight pressure and releases from the surface with negligible transfer of the adhesive to the surface. The most common examples are the adhesives used in bandages to cover wounds. Silicone pressure sensitive adhesives in particular have found use in transdermal drug delivery applications which involve the adherence of a drug-containing patch to a patient's skin, due to the fact that silicone pressure sensitive adhesives are acceptable for topical use.

In transdermal drug delivery patches, ingredients such as co-solvents and excipients have been added to the silicone pressure sensitive adhesive compositions to improve efficacy. Co-solvents are typically added to increase drug solubility in the composition, and excipients are typically added to enhance drug release from or through the composition.

However, when silicone pressure sensitive adhesives are formulated with or come in contact with co-solvents, excipients, drugs such as nicotine-based drugs, or skin penetration enhancers such as propylene glycolmonolaurate or glycerol monoleate, the silicone pressure sensitive adhesive often becomes plasticized, losing tack, adhesiveness, and resistance to flow. Such instances occur (1) in matrix-type drug delivery patches where a drug is formulated into a silicone pressure sensitive adhesive and (2) in reservoir-type drug delivery patches where a silicone pressure sensitive adhesive is on the surface of a drug delivery device containing a reservoir of a drug. In the former type of patch, the silicone pressure sensitive adhesive is in intimate contact with the drug and other possible plasticizing additives. In the latter type of patch, the silicone pressure sensitive adhesive is present to provide means for attaching the device to a patient's skin. In this device, drugs or other materials from the reservoir either pass through or otherwise may come in contact with the silicone pressure sensitive adhesive.

The problem with either device is that the additives cause reduction in cohesive strength. Cohesive strength causes the adhesive to adhere to a substrate such as a patch and prevents flow or transfer of the pressure sensitive adhesive onto either the release liner which protects the silicone pressure sensitive adhesive before use or onto the patient's skin following removal of the patch while maintaining adequate adhesion of the patch to the skin. The cohesive strengthening agent further prevents flow of the pressure sensitive adhesive beyond the edges of the patch during storage and/or use.

It is, therefore, a primary object of the invention to provide a pressure sensitive adhesive composition which has good cohesive strength and is resistant to cold flow when formulated or contacted with drugs, co-solvents, excipients or skin penetration enhancers.

SUMMARY OF THE INVENTION

A silicone pressure sensitive adhesive composition which meets the object of the invention is disclosed which is compatible with drugs, excipients, co-solvents and skin penetration enhancers while allowing for the addition of a cohesive strengthening agent to reduce cold flow. The silicone pressure sensitive adhesive comprises a silicone fluid, a silicate resin and a cohesive strengthening agent. By the addition of a cohesive strengthening agent, an improved silicone pressure sensitive adhesive is produced which retains the adhesive on the substrate, without compromising the adhesion of the adhesive to the skin of the patient wearing the bandage or patch.

In meeting the object of the invention, a silicone pressure sensitive adhesive includes a cohesive strengthening agent selected from the group consisting of nonionic surfactants, fatty acid esters of glycerol, said nonionic surfactants and said fatty acid esters being substantially insoluble in said mixture, as well as solid particulate materials selected from the group consisting of metallic salts of fatty acids, metallic salts of phosphoric acid, metallic salts of carbonic acid, polysaccharides, carboxypolymethylene, polyvinylpyrrolidone, polyvinylalcohol and amorphous precipitated silicas having a surface area of less than approximately 200 $m^2/g$ and between about 10 and 200 $m^2/g$.

BRIEF DESCRIPTION OF DRAWINGS

The nature and extent of the present invention will be clear from the following detailed description of the particular embodiments thereof, taken in conjunction with the appendant drawings, in which.

DETAILED DESCRIPTION OF THE INVENTION

Generally, the silicone pressure sensitive adhesive compositions of the present invention include a silicone pressure sensitive adhesive containing (i) a silicone fluid, (ii) a silicate resin, and (iii) a cohesive strengthening agent. The silicone pressure sensitive adhesive of the present invention includes a cohesive strengthening agent in order to overcome the problems of excessive cold flow or creep presented by the pressure sensitive adhesives of the prior art. Cold flow or creep refer to viscoelastic flow of the adhesive solids under stress. Resistance to cold flow is referred to as creep resistance. This is defined by, Carl A. Dahlquist, "Creep", *Handbook Of Pressure Sensitive Adhesive Technology* 2nd ed., (Van Nostrand Runhold, New York, N.Y., 1989), p. 97. As can be seen by the test results of the Examples below, the addition of the cohesive strengthening agents of the present invention substantially reduces cold flow. By reducing the cold flow, a superior product can be made which keeps the adhesive more on the bandage or patch, with less of the adhesive transferring to the skin of the patient wearing the bandage or transdermal patch without compromising the adhesion of the bandage to the skin of the patient. As one can remember, previous bandages left a sticky residue on the skin when it was removed. This invention alleviates this problem substantially.

I. SUITABLE SILICONE PRESSURE SENSITIVE ADHESIVES

One suitable class of silicone pressure sensitive adhesives which may be employed in the silicone pressure sensitive adhesive compositions of this invention consists of a mixture of (i) a silanol end-blocked polydiorganosiloxane fluid, e.g. a polydimethylsiloxane polymer, and (ii) a trimethylsilyl end-blocked polysilicate resin such as a silicate resin consisting of a benzene-soluble resinous copolymer containing silicon-bonded hydroxyl radicals and consisting essentially of triorganosiloxy units of the formula $R_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer, wherein each R is a monovalent organic radical independently selected from the group consisting of hydrocarbon radicals of from 1 to 6 inclusive carbon atoms. U.S. Pat. No. 2,736,721 to Dexter, et al. and U.S. Pat. No. 2,814,601, to Currie, et al. are hereby incorporated by reference to teach such or similar silicone pressure sensitive adhesives.

Another class of suitable silicone pressure sensitive adhesives for use according to this invention is that or those similar to U.S. Pat. No. 2,857,356, to Goodwin, Jr., which is also hereby incorporated by reference. The Goodwin, Jr. patent teaches silicone pressure sensitive adhesives which consist of a mixture of ingredients comprising (i) a cohydrolysis product of a trialkyl hydrolyzable silane and alkyl silicate, wherein the cohydrolysis product contains a plurality of silicon-bonded hydroxy groups, and (ii) a linear, high viscosity organopolysiloxane fluid containing silicon-bonded hydroxy groups.

The silicone fluid and the silicate resin may optionally be condensed together according to a procedure such as the procedure described in Canadian Patent 711,756 to Pail, which patent is hereby incorporated by reference. In such a condensation reaction, the silicate resin and the silicone fluid are mixed together in the presence of a catalytic amount of a silanol condensation catalyst, and then the silicate resin and the silicone fluid are condensed, for example, by heating under reflux conditions for 1 to 20 hours. Examples of silanol condensation catalysts are primary, secondary, and tertiary amines, carboxylic acids of these amines and quaternary ammonium salts.

Another class of suitable pressure sensitive adhesives to use according to the invention are those compositions described in U.S. Pat. Nos. 4,591,622 and 4,584,355 to Blizzard et al., U.S. Pat. No. 4,585,836 to Homan et al., and U.S. Pat. No. 4,655,767 to Woodard et al., which patents are hereby incorporated by reference. Generally, these pressure sensitive adhesives consist of a blend of (i) a silicate resin and (ii) a silicone fluid which are chemically treated to reduce the siliconbonded hydroxyl content of the blend. These adhesives may optionally be condensed as described immediately above prior to the chemical treatment.

In addition, the various types of silicone pressure sensitive adhesives may be blended to achieve blended characteristics. Preferably, for the greatest improvement in cohesive-strength, the silicone pressure sensitive adhesive contains some silanol radicals, preferably greater than 200 ppm, and, more preferably, greater than 400 ppm.

Typically, the most practical pressure sensitive adhesive for use in this invention includes a high molecular weight polydimethylsiloxane as the silicone fluid, since this fluid is the most economical and the most readily available of the silicone fluids.

The other adhesive component, the silicate resin, preferably has a molecular weight ranging from about 2,000 to about 4,000. The resin is employed in amounts from about 40 to about 70 parts by weight in the silicone pressure sensitive adhesive, while the silicone fluid is employed from about 60 to about 30 parts by weight, wherein the total parts of the silicate resin and the silicone fluid equal 100 parts. The silicone pressure sensitive adhesive composition contains no less than 100 ppm of silanol radicals and preferably contains between 200 ppm and 1200 ppm of silanol radicals.

The silicone pressure sensitive adhesive compositions of this invention may also contain the aforementioned ingredients: drugs, co-solvents, excipients, skin penetration enhancers or organic solvents for dissolving the silicone polymer and the silicate resin. Suitable organic solvents may have reinforcing excipients dispersed therein for dissolving the polydimethylsiloxane polymer and silicate resin, and should have a Hildebrand solubility parameter ranging from between about 5 to 10 $cal^{\frac{1}{2}}/cm^{3/2}$, and optimally between about 8 and 9 $cal^{\frac{1}{2}}/cm^{3/2}$. Examples of suitable organic solvents include aromatics such as toluene and xylene; aliphatics such as heptane and hexane; chlorinated solvents such as 1, 1, 1-trichloroethane and trichlorotrifluoroethane; fluorocarbons such as Freon 113 (Freon PCA) available from DuPont de Nemours, E. I. Co., Wilmington, Del.; aliphatic esters such as ethyl acetate; and mixtures thereof.

The silicone pressure sensitive adhesives used in this invention are not considered to be silicone adhesives which are "silicone rubbers", which generally refer to non-tacky vulcanized rubber used as structural adhesives. The most common type of silicone rubber consists of a mixture of a polydimethysiloxane gum, a filler (such as fumed silica or other inorganic, non-resinous material), a crosslinker, and optionally, a catalyst. These structural adhesives are cured to a fully rubberized state. The silicone pressure sensitive adhesives employed in this invention are tacky (or sticky) to the touch without the addition of plasticizers and typically adhere to a substrate after mild pressure is applied and therefore are referred to as pressure sensitive adhesives. The silicone pressure sensitive adhesives may be cured or "rubberized" after being mixed with the cohesive strengthening agent as discussed below. However, even after the curing, the silicone pressure sensitive adhesive composition remains tacky.

The process of curing or crosslinking silicone pressure sensitive adhesives is known in the art. For example, see "Silicone Pressure Sensitive Adhesives" by D. F. Merrill in the *Handbook Of Pressure Sensitive Adhesive Technology*, edited by D. Satas (Van Nostrand Reinhold, Florence, Ky., 1982), pages 344–352 and "Formulating Silicone Pressure Sensitive Adhesives For Application Performances" by L. A. Sobieski in *Making It Stick in '86, Advances In Pressure Sensitive Tape Technology*, seminar proceedings (Pressure Sensitive Tape Council, Deerfield, Ill., 1986), pages 1-5, both sources being hereby incorporated by reference.

Generally, however, for drug delivery applications, the silicone pressure sensitive adhesive compositions are not crosslinked because either (1) the crosslinking temperature is too high for the drugs or (2) the additives needed for crosslinking are nonbiocompatible ingredients. A silicone pressure sensitive adhesive composition is generally considered not crosslinked if it can be dissolved in a solvent.

Another difference between silicone pressure sensitive adhesives suitable for use in the present invention and unsuitable silicone rubbers lies in the fact that silicone pressure sensitive adhesives are usually fillerless or contain low amounts, e.g., less than about 5 weight %, of fillers, such as fumed silica or other inorganic reinforcing fillers known in the silicone art. On the other hand, silicone rubbers typically contain about 15-35 weight % filler. Fillers are usually not desired in high quantities in silicone pressure sensitive adhesives, because high quantities often cause the silicone pressure sensitive adhesives to lose tack and adhesiveness and to increase in viscosity, making it more difficult to apply a coating of the silicone pressure sensitive adhesive.

II COHESIVE STRENGTHENING AGENT

The cohesive strengthening agents utilized in the invention are generally insoluble in an adhesive polymer or solution, and have a mean particle size ranging from about 0.5 to about 100 microns. The melting point for the cohesive strengthening agents should be greater than about 100° C. Specifically, the cohesive strengthening agents useful for the present invention include those selected from the group consisting of: 1) nonionic surfactants; 2) fatty acid esters of glycerol; and solid particulate materials selected from the group consisting of 3) metallic salts of fatty acids; 4) metallic salts of phosphoric acid; 5) metallic salts of carbonic acid; 6) polysaccharides; 7) carboxypolymethylene; 8) polyvinylpyrrolidone; 9) polyvinylalcohol; and 10) amorphous precipitated silicas having a surface area of between about 10 and about 200 m$^2$/g, with a particle size range of between about 0.018 and 100 microns. These cohesive strengthening agents are individually described below.

1) Nonionic surfactants. Nonionic surfactants which are useful as the cohesive strengthening agent include those that are not generally soluble in the silicone pressure sensitive adhesives. Thus, they form a two-phase composition when mixed with the silicone pressure sensitive adhesive. In particular, nonionic surfactants having a hydrophilic-lipophilic balance (HLB) of between 7 and 14 are suitable. A specific example of such a surfactant is nonylphenoxypoly(ethyleneoxy)ethanol, an ethoxylated alkyl phenol that conforms generally to the formula:

$C_9H_{19}C_6H_4(OCH_2CH_2)_nOH$ where n has an average value of 9, and is sold under the trademark IGEPAL Co-630, which is owned by GAF Chemicals Corp., and is available from GAF Chemicals Corp, of Wayne, N.J. 07470. IGEPAL, Co-630 has an HLB value of about 13.

2) Fatty acid esters of glycerol. Fatty acid esters of glycerol useful as the cohesive strengthening agent generally have a high polarity and are also substantially insoluble in silicone pressure sensitive adhesives. Examples of such fatty acid esters of glycerol include cottonseed oil, corn oil, peanut oil, sesame oil, and coconut oil. These oils are oily liquids at room temperature with the exception of coconut oil which is semi-solid at room temperature.

3) Metallic salts of fatty acids. Examples of metallic salts of fatty acids which have been found suitable as cohesive strengthening agents include calcium stearate, magnesium stearate, and sodium stearate. A suitable calcium stearate is Calcium Stearate RSN ® 11-4, commercially available from Mallinckrodt Inc, St. Louis, Mo. 63147, which contains about 9-10.5 weight percent calcium oxide, has a particle size from 1.7 to 60 microns, and a specific surface area from 5.76 to 7.44 m$^2$/g. A suitable magnesium stearate is commercially available from Mallinckrodt Inc., St. Louis, Mo. 63147 and has a specific surface area from 2.45-7.93 m$^2$/g. Calcium stearate is the preferred stearate of the three stearates due to its performance in increasing cohesive strength of the silicone pressure sensitive adhesive.

4) and 5) Metallic salts of phosphoric and carbonic acid. The preferred metallic salt of phosphoric acid includes dibasic calcium phosphate, while the preferred metallic salt of carbonic acid is calcium carbonate.

6) Polysaccharides. Examples of polysaccharides which are useful as cohesive strengthening agents in the present invention include celluloses, xanthan gum, pectin, guar gum, and karaya gum. Polysaccharides contain hydroxyl radicals which are believed to be useful for bonding with the silanol radicals of the silicone pressure sensitive adhesives. Suitable polysaccharides may be celluloses which can include microcrystalline cellulose, powdered cellulose, methylcellulose, ethylcellulose, sodium carboxymethylcellulose. Microcrystalline cellulose has the general formula $(C_6H_{10}O_5)_n$, where n is about 220, with a molecular weight of about 36,000, an average particle size of about 20 to about 100 microns, and a specific surface area from about 10 to about 21 m$^2$/g. Powdered cellulose has the general formula of $(C_6H_{10}O_5)_n$, where n is about 1500, with a molecular weight of about 243,000 and a particle size of from about 1 to about 250 microns. Methylcellulose is a long chain substituted cellulose ether of about 50-1500 anhydroglycose units containing about 26-32% methoxyl groups.

7) Carboxypolymethylene. Another cohesive strengthening agent thought to be useful is carboxypolymethylene is also known as "carbomer". Generally, it is a crosslinked polymer of acrylic acid having about 0.75-2.0 weight percent polyalkylsucrose having the empirical formula: $(C_3H_4O_2)_x$. $(C_3H_5$-sucrose$)_y$ with molecular weights from about $1 \times 10^6$ to about $4 \times 10^6$.

8) Polyvinylpyrrolidones. Polyvinylpyrrolidones are also thought to be useful as the cohesive strengthening agent. They generally have the empirical formula $(C_6H_9NO)_n$, with a mean molecular weight from about 10,000 to about 700,000.

9) Polyvinylalcohol. Furthermore, polyvinylalcohols may be useful as the cohesive strengthening agent, having the empirical formula $(C_2H_4O)_n$, with an average molecular weight of from about 30,000 to about 200,000, and a melting point of about 228° C.

10) Amorphous precipitated silicas. Amorphous precipitated silicas which have been found to be especially suitable as the cohesive strengthening agents of this invention include amorphous precipitated silicas having a surface area of between about 10 and about 200 m$^2$/g, and a particle size ranging from about 0.018 to about 100 microns. One such commercially available silica is "SILENE" 732D, available from PPG Industries, Inc., Pittsburgh, Pa., owner of the trademark "SILENE". "SILENE" 732D is an amorphous precipitated hydrated silica product which typically contains about 88 weight percent silica on a dry basis and about 7 weight percent water, with an average particle size of about 0.072 microns, a BET surface area of about 30 $m^2/g$, and a pH of from about 8.5 to about 9.

Generally, the cohesive strengthening agents are insoluble in the silicone pressure sensitive adhesive, thus forming a dispersion or suspension of cohesive strengthening agent microparticles in the adhesive matrix. In addition, they are approved pharmaceutical additives. Many of the cohesive strengthening agents have the ability to hydrogen-bond to the silanol radicals of the silicone pressure sensitive adhesive due to the presence of carboxyl or hydroxyl radicals on the cohesive strengthening agents. Tests have shown that the cohesive strengthening agents of the present invention increase the viscosity of the silicone pressure sensitive adhesive at room temperature.

When mixed with the silicone fluid and silicate resin to practice this invention, the cohesive strengthening agents are desirably employed from about 1.0 to about 20.0 weight percent and, more desirably, from about 5.0 to about 15.0 weight percent based on the total weight of the silicone pressure sensitive adhesive composition. The three main components of this invention may be made by mixing the ingredients in any order. However, reaction or treatment of the ingredients, e.g., condensing according to the procedure of the previously mentioned Pail patent or chemically treating according to the previously mentioned Blizzard et al., etc. patents, may require completion prior to the addition of the cohesive strengthening agent.

Figure 1:
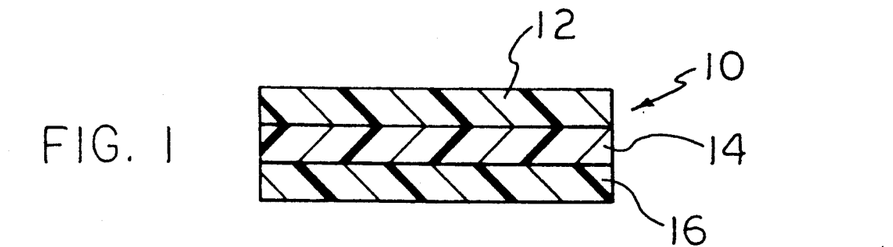
FIG. 1 shows a pressure sensitive adhesive sandwiched between a backing substrate and a release liner.

Referring now to the drawings, FIG. 1 illustrates a tape including a silicone pressure sensitive adhesive generally denoted by the numeral 10 which comprises a backing substrate 12, a pressure sensitive adhesive layer 14 and a release liner 16. This figure illustrates the basic configuration of a tape with a pressure sensitive adhesive made in accordance with the present invention. Possible uses for this embodiment are for bandages, wound dressings and medical transfer tapes. Hereinbelow are described more embodiments, with reference to the other figures.

With reference to the remaining drawings, the silicone pressure sensitive adhesive compositions of this invention are especially suitable for assisting in delivering a bioactive agent, such as a drug, to a bioactive agent-accepting substrate, such as a patient's skin. The silicone pressure sensitive adhesive compositions of this invention may be employed in three types of bioactive agent delivery modes. The first mode is a matrix-type of delivery device for the bioactive agent or drug. The matrix-type delivery device is usually a dermal patch which delivers the bioactive agent locally.

Figure 2:
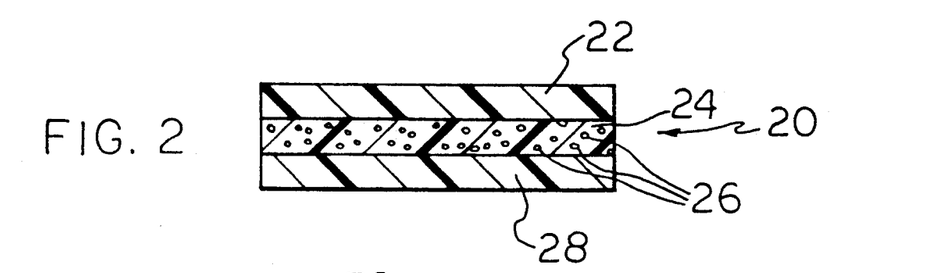
FIG. 2 shows a matrix-type delivery device for a bioactive agent or drug in place within a transdermal patch.

As shown in FIG. 2, this matrix-type delivery device is generally shown as 20 and comprises at least three layers. The first layer is a backing substrate 22 which may be permeable or occlusive to water vapor transmission from skin. The second layer is a matrix 24 atop at least portions of the backing substrate. The matrix may be one of two embodiments. In a first embodiment, as shown in FIG. 2, the matrix is made up of the silicone, creep resistant, pressure sensitive adhesive. The adhesive matrix may contain, and is compatible with compositions selected from the group consisting of drugs, excipients, enhancers, co-solvents, and mixtures thereof, shown at 26. In a second embodiment (not shown) the matrix is made up of a polymer. The polymer matrix may contain and is compatible with compositions selected from the group consisting of drugs, excipients, enhancers co-solvents, and mixtures thereof. In this second embodiment, the silicone, creep-resistant, pressure sensitive adhesive is disposed in a layer atop at least portions of the polymer matrix. The matrix is between about 1 and about 15 mils thick. The final layer is a pressure sensitive adhesive release liner 28 contacted on the matrix. The liner is between about 1 and 15 mils thick and preferably between about 5 and 10 mils thick.

The matrix-type drug delivery device as shown in FIG. 2 may include various drugs selected from the group consisting of cardiovascular agents, antiarrthymic agents, antianginal agents, antibiotics, antifungals, antimicrobials, antihypertensives, analgesics, local anesthetics, contraceptives, hormonal supplements, anti-smoking agents, appetite suppressants, hypnotics, anxiolytics and mixtures thereof. Also included may be co-solvents, enhancers and excipients selected from the group consisting of fatty acid esters, polyols, surfactants, terpenes, glycerol esters, polyethylene glycol esters, amides, sulfoxides, lactams, nonionic surfactants, sorbitan esters and mixtures thereof.

Figure 3:
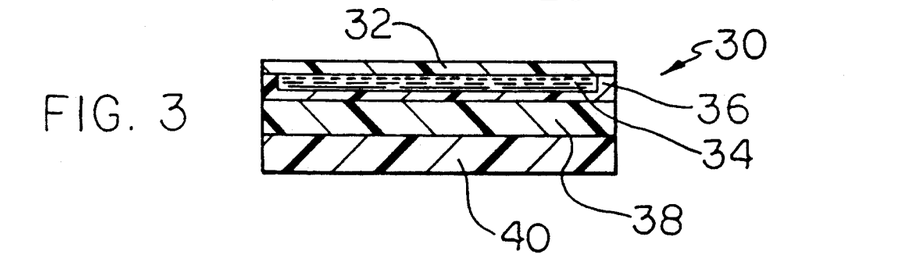
FIG. 3 shows a liquid reservoir-type transdermal drug delivery device.
Figure 4:
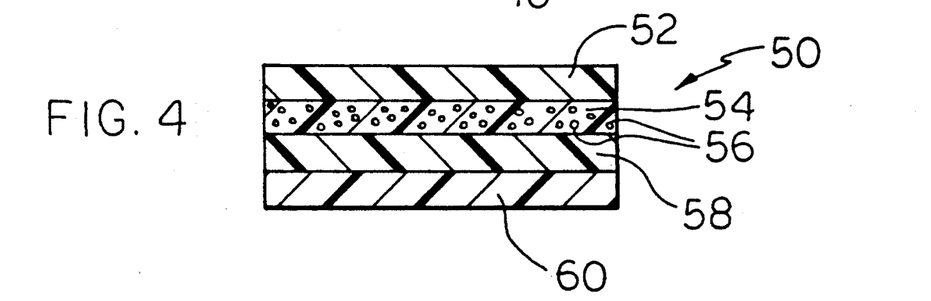
FIG. 4 shows, a solid state reservoir-type transdermal drug delivery device.

As shown in FIGS. 3 and 4, the second mode of delivery is a reservoir-type transdermal drug delivery device. Generally, this mode is applied to the skin to deliver the bioactive agent to treat systemic disease. FIG. 3 shows a liquid containing reservoir-type drug delivery device generally denoted as numeral 30 which comprises a minimum of five layers from top to bottom. The first layer 32 is a backing substrate. The second layer 34 includes a liquid reservoir which may contain bioactive agents or other compositions selected from the group consisting of drugs, excipients, enhancers, co-solvents, and mixtures thereof. The reservoir-type transdermal drug delivery device as shown in FIG. 3 may include various drugs selected from the group consisting of cardiovascular agents, antiarrthymic agents, antianginal agents, antibiotics, antifungals, antimicrobials, antihypertensives, analgesics, local anesthetics, contraceptives, hormonal supplements, anti-smoking agents, appetite suppressants, hypnotics, and anxiolytics, and mixtures thereof. Also included may be co-solvents, enhancers and excipients selected from the group consisting of fatty acid esters, polyols, surfactants, terpenes, glycerol esters, polyethylene glycol esters, amides, sulfoxides, lactams, nonionic surfactants, sorbitan esters and mixtures thereof. The third layer 36 is a rate controlling membrane positioned such that the reservoir 34 is sealed between the backing substrate 32 and the rate controlling membrane 36. This membrane acts as the rate controlling mechanism for the delivery of the liquid drug(s), co-solvents, enhancers and excipients, from the reservoir 34. The fourth layer 38 is a pressure sensitive adhesive which should be compatible with any of the drugs, excipients and co-solvents present in the liquid reservoir. The fifth layer 40 is a silicone pressure sensitive adhesive release liner. The release liner is between about 1 and 15 mils thick and preferably between about 1 and 3 mils thick. The bioactive agent of the liquid reservoir 34 may then pass from the reservoir through the attached rate controlling membrane 36 and the adhesive layer 38, and then into the skin of the patient to deliver the drug.

FIG. 4 shows a solid state reservoir-type transdermal drug delivery device. This device is denoted generally by numeral 50 and includes a first layer 52 which is a backing substrate. The second layer constitutes a solid reservoir 54 which may contain one or more bioactive agents of other compositions selected from the group consisting of drugs, excipients and co-solvents indicated at 56. The same drugs, excipients and co-solvents may be used as the liquid containing reservoir as shown in FIG. 3. The third layer of FIG. 4 is a pressure sensitive adhesive layer 58 which is compatible with the drugs, excipients and co-solvents. The fourth layer is a release liner 60. The liner 60 averages between 1 and 15 mils thick and is preferably between 1 and 3 mils thick. An additional layer (not shown) comprising a rate controlling membrane may be positioned between the solid reservoir 54 and the adhesive 58 in order to control the rate of delivery of the drug(s) and excipient(s). The surface area of both the matrix-type and reservoir-type delivery device generally ranges between 1.0 and 700 cm$^2$. This range is not to be construed as limiting, as any size device may utilized with the PSA of the present invention.

The adhesive layer of both the matrix-type and reservoir-type delivery devices, shown in FIGS. 2–4, may include one or a combination of co-solvents, enhancers and excipients which increase solubility of the drug in the adhesive matrix, enhance skin permeation to the drug, or enhance drug release from the system.

The presence of the cohesive strengthening agents in the adhesives of the present invention permits the use of drugs, excipients, co-solvents, and skin penetration enhancers which usually adversely effect the cohesive strength of prior art silicone pressure sensitive adhesives not containing any cohesive strengthening agents. Preferably, the cohesive strengthening agents have a melting point of greater than 40° C. and a Hildebrand solubility parameter between about 5 and 15 cal$^{1/2}$/cm$^{3/2}$. The addition of the cohesive strengthening agents taught herein significantly reduces flow and improves creep resistance of silicone adhesives utilized to deliver a bioactive agent, such as a drug to a substrate, such as a patient's skin.

The following examples of the invention are meant to be illustrative only and should not be construed as limiting the invention which is properly delineated in the appended claims. In the following examples, all parts and percentages are by weight unless otherwise specified.

EXAMPLES

The basic silicone pressure sensitive adhesive prepared without the cohesive strengthening agent may be prepared as follows. Once this basic formulation was prepared, Examples A-F were made by adding various cohesive strengthening agents, testing them and tabulating the results.

The basic adhesive formulations include two main components: a silicate resin and a silicone fluid. In this preparation, we will be discussing Adhesives I, II, and III. They are made from various combinations of Resins A-1, A-2 and trimethylsiloxy end-blocked polydimethylsiloxane (PDMS) Fluid A as described below.

Resin A-1 is a xylene solution of a resinous copolymeric siloxane prepared from 45 parts of sodium silicate and 20 parts of Me$_3$SiCl (Me=CH$_3$) according to the method of U.S. Pat. No. 2,676,182 to Daudt, et al., which is hereby incorporated by reference, and contains Me$_3$SiO$_{\frac{1}{2}}$ units and SiO$_{4/2}$ units in a ratio of approximately 0.75:1.0, and has a nonvolatile content typically about 69–71%, an acid number in the range of 0.3 to 1.4, a viscosity in the range of 10–14 centipoise at 25° C. in hexane solution, and a silicon-bonded hydroxyl content of about 2.5 weight percent based on a 100% non-volatilized content and a number average molecular weight range of between 2,000 to 4,000.

Resin A-2 is Resin A-1 which has been devolatilized (100% non-volatile content).

PDMS Fluid A is a homogeneous mixture of a hydroxyl end-blocked polydimethylsiloxane having a number-average molecular weight range of between 40,000 to 100,000 with minor amounts of cyclic polydimethylsiloxane having degrees of polymerization between 4 and 30, the mixture having a viscosity between 12,000 and 15,000 centipoise as measured using a Brookfield Viscometer Model HAF with spindle #3 at 10 RPM's.

Adhesive I, a 50 wt % solution of a high silanol containing silicone pressure sensitive adhesive in xylene solvent was prepared by homogeneously mixing 34.0 parts by weight of Resin A-2, 34.0 parts by weight xylene, and 31.0 parts by weight PDMS Fluid A. The mixture was then heated to 100° C. and anhydrous ammonia was passed through the mixture at a rate of 11 ml/min/lb of non-volatile component of the mixture for approximately 2 hours. The mixture was then stripped to greater than 99% non-volatile content and redissolved in hexane to a non-volatile content of 50 wt %.

Adhesive II, a 50 wt % solution of a low silanol containing silicone pressure sensitive adhesive in xylene solvent, was prepared by homogeneously mixing 34.0 parts by weight of Resin A-2, 34.0 parts by weight hexane, and 31.0 parts by weight PDMS Fluid A. The mixture was then heated to 100° C. and anhydrous ammonia was passed through the mixture at a rate of approximately 11 ml/min/lb. of nonvolatile component of the mixture for approximately 2 hours. To endcap the mixture, hexamethyldisilazane was then admixed at a 3:1 mole ratio of end-blocking triorganosilyl to total silicon-bonded hydroxyl radicals present in the resin copolymer and polydiorganosiloxane, and the mixture was allowed to react for 3 hours at 95°–100° C. The mixture was then heated to 140° C. and maintained at 140° C. under reflux conditions for 3 hours to remove condensation water. The mixture was then stripped to greater than 99% non-volatile contents, and redissolved in hexane to a non-volatile content of 50 wt %.

Adhesive III, a 50 wt % solution of a high silanol-containing silicone pressure sensitive adhesive in Freon PCA solvent was prepared as described for Adhesive I, except, after stripping, it was redissolved in Freon PCA to a non-volatile content of 50 wt %.

Preferably, the silicone pressure sensitive adhesives formed by this invention have tack values ranging between about 50 and about 800 grams; peel values between about 0.5 and 50 g/cm; adhesion values between about 200 and 2000 g/cm; a dynamic viscosity of between about $1 \times 10^5$ and $1 \times 10^8$ poise; loss modulus between about $1 \times 10^5$ and $1 \times 10^7$ dyne/cm$^2$, and a loss tangent between about 0.2 and 1.0 at a sweep frequency of 1 rad/sec on a 1 mm thick sample at room temperature.

Creep was also measured. As stated hereinabove, creep is a measure of viscoelastic flow of the adhesive solids.

A general method for measuring the values for tack, peel force and adhesion is described here. Although the following Examples utilize different chemical compositions, the following testing methods were followed for all samples. Measurements were obtained through testing a one inch wide polyester tape having a silicone pressure sensitive adhesive thereon prepared by blending about 5 percent calcium stearate with about 90% by weight solution of silicone pressure sensitive adhesive and casting it to a 5 mil thickness on "SCOTCHPAK" 1022 Release Liner, a polyester film coated with a release coating available from the 3M Company, St. Paul, Minn., owner of the trademark "SCOTCHPAK", 3M Company Health Care Specialties Div. St. Paul Minn. After coating, a sheet strip of "MYLAR" polyester film, 5 mils thick, is adhered to each coated sample with a 4.5 lb. rubber transfer roller. Laminated sheets were then cut into 1 inch wide strips.

The tack values were measured using a "POLYKEN" Probe Tack Tester, Series 400, made by Testing Machines, Inc., Amityville, N.Y. The speed of the probe was controlled at 1.0 cm/second and the dwell time of the probe was 1.0 seconds. Tack values of between about 50 and about 800 grams are considered acceptable. Test results for the tack values of this Example of a calcium stearate containing adhesive are set forth in Table C2 and range between 144 ($\pm$16) grams and 182 ($\pm$84) grams, well within the desirable range.

Peel values were obtained by stripping the tape from the "SCOTCHPAK" 1022 Release Liner at a rate of 40 inches/minute at an angle of 180° while attached to a tensile testing machine. An average value over the entire length of the liner was recorded. Peel values of less than 50 g/cm were considered acceptable. These peel values are set forth in Table C2 and were between 0.70 ($\pm$0.20) and 4.50 ($\pm$0.10) g/cm for all samples, again, within the acceptable values of less than 50 g/cm.

Adhesion values were obtained as follows. The calcium stearate containing silicone pressure sensitive adhesive composition was adhered to a stainless steel panel with a 4.5 lb. roller and allowed to equilibrate for 15 minutes. The adhesion measurements were obtained by stripping each tape from the panel at a rate of 12 inches/minute at an angle of 180° while attached to a tensile testing machine. Adhesion values were low but remained within the desirable range of between about 100 and about 2000. As shown in Table C2, adhesion values ranged from 134 ($\pm$33) to 154 ($\pm$14.5) g/cm.

Shear values were measured by cutting three strips of the prepared laminates 2.5 cm wide and 7.5 cm in length. A 3.5 cm wide by 5.0 cm long strip of Mylar, a polyester film available from DuPont de Nemours, E. I Co., Wilmington Del. also owner of the trademark "Mylar", is applied to the adhesive strip so as to provide an overlap of 2.5 cm in the lengthwise direction. These are laminated using a 4.5 lb. rubber roller and allowed to equilibrate for 20 minutes. The specimen is mounted into the jaws of the Instron and pulled at a speed of 0.5 cm/min. and the peak load required to shear and separate the laminate is recorded in kg.

Desirable values range between 15-25 kg. As shown in Table C2, values ranged from 18.0 ($\pm$0.8) to 23.9 ($\pm$0.0) kg, and were within the acceptable range.

Hereinbelow, the term "pressure sensitive adhesive" may be abbreviated to "PSA".

EXAMPLE A

Improved Creep Resistant Silicone Pressure Sensitive Adhesive Containing Calcium Stearate Adhesive formulations with various levels (0.0, 2.5, 5.0, and 10.0 grams) of calcium stearate in a silicone pressure sensitive adhesive were prepared as follows. As shown in Table A, Adhesive I was mixed with varying amounts of calcium stearate (Table A1). The formulations were poured onto a polyester release liner (SCOTCHPAK ® 1022 Fluoropolymer coated liner, 3M Company, St. Paul, Minn. 55144) and the solvent was allowed to evaporate at room temperature (25° C.) for a minimum of 24 hours. The resultant compositions were evaluated for creep resistance by taking an 11 gram sample of each formulation (N=3) and placing it into wells (0.9 cm. deep, 3.8 cm. in diameter) in a test apparatus consisting of a series of wells at the top of an aluminum block measuring 18 inches wide, 14 inches tall and 1 inch thick. The adhesive was formed to fit into individual test wells, and the entire test apparatus was placed in a 125° C. oven in a horizontal position for 15 min. to soften the adhesive. The test apparatus was removed and the individual pieces of the adhesive were pressed flat to form disks measuring about 0.9 cm. × 3.8 cm. and pressed onto an aluminum plate and then placed in a vertical position in the oven maintained at 125° C. The distance the adhesive flowed down the vertical surface of the aluminum plate was measured periodically to determine flow or creep.

The effectiveness of calcium stearate in reducing flow and imparting creep resistance of the silicone adhesive is shown in Table A2. Calcium stearate provided reinforcement of the silicone adhesive, reduced flow and imparted creep resistance proportional to its loading level in the adhesive. The results on Table A2 show that adding calcium stearate was effective over the range of <5 wt. % to 20 wt. % with the preferred range being between 1 to 10 wt %. Standard deviations are based on 3 replicates of each sample (signified by N=3).

TABLE A1

ADHESIVE I CONTAINING CALCIUM STEARATE

| Formulation Number | Adhesive I[a] WT % | Adhesive I[a] Grams | Calcium Stearate Grams | Calcium Stearate WT % Solution | Calcium Stearate WT % Tape |
|---|---|---|---|---|---|
| 1 | 100 | 100 | 0 | 0 | 0 |
| 2 | 95 | 95 | 2.5 | 2.6 | 5 |
| 3 | 90 | 90 | 5.0 | 5.3 | 10 |
| 4 | 80 | 80 | 10.0 | 11.1 | 20 |

[a]Adhesive I is a 50 wt % solution of a high silanol containing adhesive in hexane solvent.

TABLE A2

EFFECT OF CALCIUM STEARATE ON FLOW OF ADHESIVE I

| Formulation Number | Calcium Stearate WT % | Flow in inches[a] Time In Minutes Mean +/− SD, N = 3[b] 15 | 30 | 45 | 60 | Maximum flow after 60 min. |
|---|---|---|---|---|---|---|
| 1 | 0 | 1.20 +/− 0.06 | 2.10 +/− 0.10 | 2.93 +/− 0.15 | 3.70 +/− 0.10 | 3.70 +/− 0.10 |

TABLE A2-continued
EFFECT OF CALCIUM STEARATE ON FLOW OF ADHESIVE I

| Formulation Number | Calcium Stearate WT % | Flow in inches[a] Time In Minutes Mean +/− SD, N = 3[b] | | | | Maximum flow after 60 min. |
|---|---|---|---|---|---|---|
| | | 15 | 30 | 45 | 60 | |
| 2 | 5  | 0.10 +/− 0.00 | 0.30 +/− 0.00 | 0.57 +/− 0.03 | 1.05 +/− 0.05 | 1.05 +/− 0.05 |
| 3 | 10 | 0.07 +/− 0.03 | 0.22 +/− 0.03 | 0.38 +/− 0.03 | 0.65 +/− 0.05 | 0.65 +/− 0.05 |
| 4 | 20 | 0.05 +/− 0.00 | 0.13 +/− 0.03 | 0.20 +/− 0.00 | 0.25 +/− 0.00 | 0.25 +/− 0.00 |

[a]Flow was evaluated by placing an 11 gram sample of adhesive, 3.8 cm. diameter and 0.9 cm. thick, onto a vertical aluminum surface in an oven maintained at 125° C.
[b]N = Number of replicates for each formulation, upon which standard deviation is based.

EXAMPLE B
Improved Creep Resistant Amine-Compatible, Low Silanol Containing Silicone Adhesive By Co-Formulating With a Non-Amine Compatible High Silanol Silicone Adhesive An adhesive formulation consisting of a low silanol containing amine-compatible silicone adhesive, Adhesive II, and a high silanol containing silicone adhesive, Adhesive I, was prepared as shown in Table B1. The adhesive solutions were blended to homogeneity and poured onto a polyester release liner (SCOTCH-PAK® 1022 Fluoropolymer Coated Liner, 3M company, St. Paul, Minn. 55144). The solvent was allowed to evaporate at room temperature (25° C.) for a minimum of 24 hours before testing.

These compositions were evaluated for flow reduction and creep resistance by the same method as outlined in Example A.

Adhesive II has lower cohesive strength, and exhibits significantly more flow when compared to Adhesive I. In many cases this is a disadvantage where an amine-compatible adhesive is required. By combining Adhesive I with Adhesive II, a significant reduction of flow and improved creep resistance was achieved. This is significant since reinforcing excipients such as calcium stearate are not effective in reducing flow of Adhesive II, the low silanol containing, amine-compatible Adhesive.

TABLE B1
BIO-PSA SILICONE ADHESIVES

| Formulation Number | Adhesive I[a] | | Adhesive II[b] | |
|---|---|---|---|---|
| | WT % | Grams | WT % | Grams |
| 1 | 100 | 100 | 0 | 0 |
| 2 | 0 | 0 | 100 | 100 |
| 3 | 50 | 50 | 50 | 50 |

[a]Adhesive I is a 50 wt % solution of a high silanol containing adhesive in hexane solvent.
[b]Adhesive II is a 50 wt % solution of a low silanol containing amine-compatible adhesive in hexane solvent.

EXAMPLE C
Stability of Improved Creep Resistant Silicone Pressure Sensitive Adhesive Containing Calcium Stearate This example details a stability and shelf-life test for similar formulations as in Example A. A formulation of a creep resistant silicone pressure sensitive adhesive was prepared by blending calcium stearate with a solution of a silicone pressure sensitive adhesive and cast to form a tape whose properties (e.g. tack, peel, adhesion and shear strength) were evaluated initially and after 1 and 3 months.

Adhesive I was mixed with varying amounts of calcium stearate (0 and 5 grams) as shown on Table C1. The silicone adhesive solutions with and without calcium stearate were cast onto a polyester release liner (SCOTCHPAK® 1022 Fluoropolymer coated Liner, 3M Company, St. Paul, Minn. 55144), and allowed to air dry at room temperature (25° C.) for 30 minutes to achieve a dry film thickness of 3 to 4 mils. The dried adhesive/release liner was then laminated on a 5 mil sheet of polyester using a 4.5 lb. rubber transfer roll.

Tapes were stored at room temperature (25° C.) and tested initially (after 2 weeks) and after 1 and 3 months to evaluate the stability of the adhesives.

Tape properties important to the performance of adhesives used in a transdermal drug delivery tape such as tack, peel, adhesion, and shear strength were evaluated and were found to be very good. Results of these studies are shown in Table C2. The control adhesive possesses tack, peel, adhesion and shear strength values suitable for use as an adhesive to affix a transdermal drug delivery device to the skin. The test results show that these values were stable over the 3 month period.

Incorporation of calcium stearate into the adhesive produces a desirable slight increase in tack properties and a slight decrease in adhesion values. Although peel values generally increase slightly over time, values less than 50 g/cm are considered acceptable. The data shows values greatly below this acceptable value.

This data demonstrates that calcium stearate is compatible with a high silanol containing silicone adhesive

TABLE B2
EFFECT OF ADHESIVE I ON COLD FLOW OF ADHESIVE II

| Formulation Number | Adhesive | Flow in inches[a] Time In Minutes Mean +/− SD, N = 3[b] | | | | Maximum flow after 60 min. |
|---|---|---|---|---|---|---|
| | | 15 | 30 | 45 | 60 | |
| 1 | I | 0.06 +/− 0.10 | 1.40 +/− 0.20 | 2.30 +/− 0.20 | 2.80 +/− 0.20 | 2.80 +/− 0.20 |
| 2 | II | 2.70 +/− 0.20 | 4.70 +/− 0.20 | 6.50 +/− 0.30 | 7.80 +/− 0.10 | 7.80 +/− 0.10 |
| 3 | I & II (1:1) | 1.50 +/− 0.10 | 2.30 +/− 0.10 | 3.20 +/− 0.20 | 4.20 +/− 0.20 | 4.20 +/− 0.20 |

[a]Flow was evaluated by placing an 11 gram sample of adhesive, 3.8 cm. diameter and 0.9 cm. thick, onto a vertical aluminum surface in an oven maintained at 125° C.
[b]N = Number of replicates for each sample, upon which standard deviation is based.

at levels as high as 10 wt. % and results in useful pressure sensitive adhesive compositions which exhibit an acceptable stability over time.

TABLE C1

ADHESIVE I CONTAINING CALCIUM STEARATE

| Formulation Number | Adhesive I[a] WT % | Grams | Calcium Stearate Grams | WT % Solution | WT % Tape |
|---|---|---|---|---|---|
| 1 | 100 | 100 | 0 | 0 | 0 |
| 2 | 90 | 90 | 5.0 | 5.3 | 10 |

[a]Adhesive I is a 50 wt % solution of a high silanol containing adhesive in hexane solvent.

TABLE C2

STABILITY OF IMPROVED CREEP RESISTANT TAPES PREPARED FROM ADHESIVE I CONTAINING CALCIUM STEARATE

| Formulation Number | Excipient Wt % | Time Weeks (Months) | Tape Properties Mean +/− SD, N = 3[a] | | | |
|---|---|---|---|---|---|---|
| | | | Tack (grams) | Peel (g/cm) | Adhesion (g/cm) | Shear (kg) |
| 1 | Control Adhesive I | 2 (1) (3) | 135 +/− 18 143 +/− 35 126 +/− 25 | 0.80 +/− 0.11 0.90 +/− 0.15 5.20 +/− 1.10 | 706 +/− 348 725 +/− 93 718 +/− 105 | 23.8 +/− 0.1 22.4 +/− 0.7 17.3 +/− 3.6 |
| 2 | Adhesive I+ 10 WT % Calcium Stearate | 2 (1) (3) | 156 +/− 27 144 +/− 16 182 +/− 84 | 0.80 +/− 0.11 0.70 +/− 0.20 4.50 +/− 0.10 | 137 +/− 33 134 +/− 33 154 +/− 14.5 | 23.9 +/− 0.0 21.9 +/− 0.1 18.0 +/− 0.8 |

[a]N = Number of replicates for each sample, upon which standard deviation is based.

EXAMPLE D

Matrix-Type Transdermal Drug Delivery Patches Prepared From a Creep Resistant Silicone Pressure Sensitive Adhesive Transdermal adhesive matrix-type patches were prepared containing 5 wt. % 17-Beta estradiol and either 0, 4, or 8 wt. % of the skin penetration enhancer propylene glycolmonolaurate (PGML) using a high silanol containing silicone adhesive (Adhesive III) without calcium stearate (control) and a high silanol containing silicone adhesive, Adhesive I with 10 wt. % calcium stearate as a reinforcing filler (Table D1).

The adhesive solution was cast onto a polyester release liner (SCOTCHPAK® 1022 Fluoropolymer Coated Liner, 3M Company, St. Paul, Minn. 55144) and was allowed to air dry at 25° C. resulting in a matrix 5 mil thick. This was then laminated onto a polyester film and die cut into 4 cm. diameter patches. Transdermal patches containing 10 wt. % calcium stearate as a reinforcing filler were evaluated subjectively after 1 week for functional properties including the force required to remove the release liner, finger tack, and adhesion to the ventral forearm.

Results of these subjective evaluations are shown in Table D2. The force required to remove the release liner from all patch formulations was low and acceptable. Acceptable moderate to high tack was evident and good skin adhesion was observed initially after applying the patch to the ventral forearm demonstrating the suitable functional adhesive properties of these creep resistant silicone adhesive matrix-type transdermal patches.

TABLE D1

TRANSDERMAL PATCHES CONTAINING 5 WT % ESTRADIOL AND VARIOUS LEVELS OF A SKIN ENHANCER-PROPYLENE GLYCOL MONOLAURATE (PGML)

| Formulation Number | Adhesive | PGML WT % | Estradiol WT % | Calcium[a] Stearate WT % |
|---|---|---|---|---|
| 1 | III | 0 | 5 | 0 |
| 2 | III | 4 | 5 | 0 |
| 3 | III | 8 | 5 | 0 |
| 4 | I | 0 | 5 | 10.0 |
| 5 | I | 4 | 5 | 10.0 |
| 6 | I | 8 | 5 | 10.0 |

[a]Where the reinforcing agent is calcium stearate (cs) formulated with Adhesive I.

TABLE D2

SUBJECTIVE MEASUREMENT OF PEEL, TACK AND SKIN ADHESIVE PROPERTIES OF TRANSDERMAL PATCHES[a] CONTAINING 5 WT % ESTRADIOL AND VARIOUS LEVELS OF SKIN ENHANCER PROPYLENE GLYCOL MONOLAURATE (PGML)

| Formulation Number | PGML[b] WT % | Excipient[c] WT % | Subjective Properties[d] | | |
|---|---|---|---|---|---|
| | | | Peel Force | Finger Tack | Skin Adhesion |
| 4 | 0 | 10 | 1 | 3 | 3 |
| 5 | 4 | 10 | 2 | 4 | 3 |
| 6 | 8 | 10 | 3 | 4 | 4 |

[a]Pressure sensitive adhesive matrix contains 5 wt % estradiol.
[b]Propylene glycol monolaurate (PGML).
[c]Calcium stearate (cs) as a reinforcing filler.
[d]Subjective adhesive properties:
0 = none
1 = very slight
2 = slight
3 = moderate
4 = high

EXAMPLE E

Creep Resistance of Matrix-Type Transdermal Drug Delivery Patches

The viscoelastic properties of the transdermal drug delivery matrix-type patches prepared in Example D were evaluated on a dynamic spectrometer (Rheometrics Dynamic spectrometer, Model RMS 800, Rheometrics Inc., Piscataway, N.J. 08854). The adhesive matrix from patches was transferred to 25 mm. diameter parallel plates and built up to a thickness of 1.0 mm. Properties of adhesive composition were characterized between an angular frequency sweep of from 0.1 to 100 rad/sec and 30° C. at less or equal to 10 percent strain.

The following viscoelastic parameters were evaluated as a function of frequency:
1. Elastic Storage Modulus (G', dyne/cm$^2$)
2. Dynamic Viscosity (Poise)

The viscoelastic properties of the transdermal adhesive matrix with and without calcium stearate characterized at a sweep frequency of 0.1 rad/sec or 100 rad/sec are shown in Tables E1 and E2, respectively.

Formulation of skin penetration enhancers such as propylene glycol monolaurate (PGML) into the silicone adhesive has a plasticizing effect on the adhesive and increases flow properties. As the weight percent loading of the skin penetration enhancer (PGML) is increased in the silicone adhesive matrix, the storage modulus (G'), loss modulus (G") and, dynamic viscosity decreased while the loss tangent (TAN-DELTA, G"/G') increased.

Formulation of 10 wt. % calcium stearate in the matrix containing 5 wt. % 17-Beta Estradiol resulted in improved creep resistance as reflected by a higher storage modulus (G'), loss modulus (G") and dynamic viscosity and lower loss tangent (TAN-DELTA, G"/G') compared to the same drug containing adhesive matrix without calcium stearate.

Formulation of 10 wt. % calcium stearate in the adhesive matrix containing drug and skin penetration enhancer counteracted the plasticizing effect of PGML and resulted in an improvement in the viscoelastic properties of the silicone adhesive matrix (e.g. 4 wt. % PGML) at both low and high strain rates (e.g. 0.1 rad/sec. as shown in Table E1 and 100 rad/sec. in Table E2).

under the trademark Ethocel, Type 46080, owned by Dow Chemical, Midland, Mich., and magnesium stearate sold under the trademark Hy-Qual NF Impalpable Powder, owned by Mallinckrodt, Inc, Lodi, N.J., were formulated with Adhesive I as shown in Table F1 and processed and evaluated for creep resistance as outlined in Example A.

Although Carbopol 934P is a pharmaceutical excipient useful for its thixotropic properties and increasing viscosity of pharmaceutical formulations, it was surprisingly not effective in reducing the flow properties of the high silanol containing silicone adhesive.

Ethyl cellulose, also useful as a thickening agent with a greater hydrogen bonding potential, was very effective in reducing the flow properties of the high silanol containing silicone adhesive proportional to its loading level in the adhesive. The preferable loading level of ethyl cellulose in the silicone adhesive was found to be between about 10 and 20 wt. percent.

Surprisingly, magnesium stearate which is a pharmaceutical excipient used as a lubricant in oral dosage forms, was also found to be very effective in reducing the flow properties of the high silanol containing silicone adhesive when formulated at levels of 10 to 20 wt. percent.

TABLE E1

VISCOELASTIC PROFILE OF A TRANSDERMAL DRUG DELIVERY SILICONE PRESSURE SENSITIVE ADHESIVE MATRIX AT A FREQUENCY OF 0.1 RAD/SEC

| Formulation Number | Adhesive | PGML[a] WT % | Calcium[b] Stearate | Storage Modulus DYNE/CM$^2$ × 10$^{-5}$ | Loss Modulus DYNE/CM$^2$ × 10$^{-6}$ | Dynamic Viscosity Poise × 10$^{-7}$ | Loss Tangent |
|---|---|---|---|---|---|---|---|
| 1 | III | 0 | 0 | 9.95 | 1.350 | 1.680 | 1.36 |
| 2 | III | 4 | 0 | 0.45 | 0.080 | 0.090 | 1.76 |
| 3 | III | 8 | 0 | 0.17 | 0.030 | 0.040 | 1.76 |
| 4 | I | 0 | 10 | 32.10 | 2.740 | 4.220 | 0.85 |
| 5 | I | 4 | 10 | 1.83 | 0.290 | 0.340 | 1.58 |
| 6 | I | 8 | 10 | 0.26 | 0.040 | 0.050 | 1.70 |

[a]Propylene glycol monolaurate (PGML), a skin penetration enhancer.
[b]Pressure sensitive adhesive matrix contains 5 wt % estradiol and 0 or 10 wt % calcium stearate as a reinforcing filler (cs) in a high silanol containing silicone psa.

TABLE E2

VISCOELASTIC PROFILE OF A TRANSDERMAL DRUG DELIVERY SILICONE PRESSURE SENSITIVE ADHESIVE MATRIX AT A FREQUENCY OF 100 RAD/SEC

| Formulation Number | Adhesive | PGML[a] WT % | Calcium[b] Stearate | Storage Modulus DYNE/CM$^2$ × 10$^{-5}$ | Loss Modulus DYNE/CM$^2$ × 10$^{-6}$ | Dynamic Viscosity Poise × 10$^{-7}$ | Loss Tangent |
|---|---|---|---|---|---|---|---|
| 1 | III | 0 | 0 | 1.00 | 2.42 | 1.03 | 0.24 |
| 2 | III | 4 | 0 | 0.42 | 2.52 | 0.49 | 0.59 |
| 3 | III | 8 | 0 | 0.11 | 1.07 | 0.15 | 0.98 |
| 4 | I | 0 | 10 | 1.16 | 2.43 | 1.18 | 0.21 |
| 5 | I | 4 | 10 | 0.69 | 2.85 | 0.74 | 0.41 |
| 6 | I | 8 | 10 | 0.16 | 1.42 | 0.21 | 0.89 |

[a]Propylene glycol monolaurate (PGML), a skin penetration enhancer.
[b]Pressure sensitive adhesive matrix contains 5 wt % estradiol and 0 or 10 wt % calcium stearate as a reinforcing filler (cs) in a high silanol containing silicone psa.

EXAMPLE F

Improved Creep Resistant Silicone Pressure Sensitive Adhesive Containing Reinforcing Excipients Various levels of polyacrylic acid sold under the trademark Carbopol 934P, owned by B.F. Goodrich Chemical Group, Cleveland, Ohio, ethyl cellulose sold

TABLE F1

ADHESIVE CONTAINING PHARMACEUTICAL EXCIPIENTS

| Formulation Number | Adhesive I[a] WT % | Adhesive I[a] Grams | Excipients[b] Type | Excipients[b] Grams | WT % Solution | WT % Tape |
|---|---|---|---|---|---|---|
| 1 | 100 | 100 | — | — | — | — |
| 2 | 99.5 | 99 | ca | 0.5 | 0.5 | 1 |
| 3 | 97.4 | 95 | ca | 2.5 | 2.6 | 5 |

TABLE F1-continued

ADHESIVE CONTAINING PHARMACEUTICAL EXCIPIENTS

| Formulation Number | Adhesive I[a] WT % | Adhesive I[a] Grams | Excipients[b] Type | Excipients[b] Grams | WT % Solution | WT % Tape |
|---|---|---|---|---|---|---|
| 4 | 94.7 | 90 | ca | 5.0 | 5.3 | 10 |
| 5 | 88.9 | 80 | ca | 10.0 | 11.1 | 20 |
| 6 | 99.5 | 99 | ec | 0.5 | 0.5 | 1 |
| 7 | 97.4 | 95 | ec | 2.5 | 2.6 | 5 |
| 8 | 94.7 | 90 | ec | 5.0 | 5.3 | 10 |
| 9 | 88.9 | 80 | ec | 10.0 | 11.1 | 20 |
| 10 | 99.5 | 99 | ms | 0.5 | 0.5 | 1 |
| 11 | 97.4 | 95 | ms | 2.5 | 2.6 | 5 |
| 12 | 94.7 | 90 | ms | 5.0 | 5.3 | 10 |
| 13 | 88.9 | 80 | ms | 10.0 | 11.1 | 20 |

[a]Adhesive I is a 50 wt % solution of a high silanol containing silicone adhesive in hexane solvent.
[b]Excipients include Carbopol 934P (ca), ethyl cellulose (ec), and magnesium stearate (ms).

TABLE F2

EFFECT OF CARBOPOL 934P ON FLOW OF ADHESIVE I

| Formulation Number | WT % Carbopol 934 | Flow in inches[a] Time In Minutes Mean +/- SD, N = 3[b] 15 | 30 | 45 | 60 | Maximum flow after 60 min. |
|---|---|---|---|---|---|---|
| 1 | 0 | 0.09 +/- 0.05 | 0.34 +/- 0.08 | 0.08 +/- 0.17 | 1.40 +/- 0.30 | 1.40 +/- 0.30 |
| 6 | 1 | 0.28 +/- 0.08 | 1.07 +/- 0.31 | 1.85 +/- 0.35 | 2.67 +/- 0.50 | 2.67 +/- 0.50 |
| 7 | 5 | 0.22 +/- 0.03 | 0.00 +/- 0.15 | 1.35 +/- 0.22 | 1.98 +/- 0.33 | 1.98 +/- 0.33 |
| 8 | 10 | 0.23 +/- 0.06 | 0.60 +/- 0.15 | 1.52 +/- 0.42 | 2.47 +/- 0.42 | 2.47 +/- 0.42 |
| 9 | 20 | 0.20 +/- 0.00 | 0.55 +/- 0.06 | 1.27 +/- 0.10 | 2.20 +/- 0.05 | 2.20 +/- 0.05 |

[a]Flow was evaluated by placing an 11 gram sample of adhesive, 3.8 cm. diameter and 0.9 cm. thick, onto a vertical aluminum surface in an oven maintained at 125° C.
[b]N = Number of replicates for each sample, upon which standard deviation is based.

TABLE F3

EFFECT OF ETHYL CELLULOSE ON FLOW OF ADHESIVE I

| Formulation Number | WT % Ethyl Cellulose | Flow in inches[a] Time In Minutes Mean +/- SD, N = 3[b] 15 | 30 | 45 | 60 | Maximum flow after 60 min. |
|---|---|---|---|---|---|---|
| 1 | 0 | 0.09 +/- 0.05 | 0.34 +/- 0.08 | 0.80 +/- 0.17 | 1.40 +/- 0.30 | 1.40 +/- 0.30 |
| 6 | 1 | 0.13 +/- 0.06 | 0.47 +/- 0.08 | 1.10 +/- 0.20 | 1.88 +/- 0.31 | 1.88 +/- 0.31 |
| 7 | 5 | 0.15 +/- 0.09 | 0.42 +/- 0.10 | 0.80 +/- 0.17 | 1.33 +/- 0.28 | 1.33 +/- 0.28 |
| 8 | 10 | 0.10 +/- 0.06 | 0.28 +/- 0.08 | 0.58 +/- 0.08 | 0.98 +/- 0.16 | 0.98 +/- 0.16 |
| 9 | 20 | 0.10 +/- 0.06 | 0.10 +/- 0.00 | 0.50 +/- 0.08 | 0.77 +/- 0.06 | 0.77 +/- 0.06 |

[a]Flow was evaluated by placing an 11 gram sample of adhesive, 3.8 cm. diameter and 0.9 cm. thick, onto a vertical aluminum surface in an oven maintained at 125° C.
[b]N = Number of replicates for each sample, upon which standard deviation is based.

TABLE F4

EFFECT OF MAGNESIUM STEARATE ON FLOW OF ADHESIVE I

| Formulation Number | WT % Magnesium Stearate | Flow in inches[a] Time In Minutes Mean +/- SD, N = 3[b] 15 | 30 | 45 | 60 | Maximum flow after 60 min. |
|---|---|---|---|---|---|---|
| 1 | 0 | 0.09 +/- 0.05 | 0.34 +/- 0.08 | 0.80 +/- 0.17 | 1.40 +/- 0.30 | 1.40 +/- 0.30 |
| 10 | 1 | 0.32 +/- 0.03 | 0.83 +/- 0.06 | 1.43 +/- 0.06 | 2.07 +/- 0.12 | 2.07 +/- 0.12 |
| 11 | 5 | 0.15 +/- 0.09 | 0.42 +/- 0.10 | 0.80 +/- 0.17 | 1.33 +/- 0.28 | 1.33 +/- 0.28 |
| 12 | 10 | 0.13 +/- 0.05 | 0.33 +/- 0.06 | 0.57 +/- 0.03 | 0.85 +/- 0.05 | 0.85 +/- 0.05 |
| 13 | 20 | 0.05 +/- 0.06 | 0.10 +/- 0.00 | 0.40 +/- 0.08 | 0.50 +/- 0.0 | 0.50 +/- 0.05 |

[a]Flow was evaluated by placing an 11 gram sample of adhesive, 3.8 cm. diameter and 0.9 cm. thick, onto a vertical aluminum surface in an oven maintained at 125° C.
[b]N = Number of replicates for each sample, upon which standard deviation is based.

I claim:

1. A matrix transdermal drug delivery device, comprising:
    (a) a backing substrate;
    (b) a matrix containing a silicone, creep resistant, pressure sensitive adhesive atop at least portions of said backing substrate, the silicon pressure sensitive adhesive comprising (i) from about 60 to about 30 parts by weight of a silicon fluid; (ii) from about 40 to about 70 parts by weight of a silicate resin, wherein the total parts of the silicone fluid and silicate resin equal 100 parts; and (iii) from about 1.0 to about 20.0 weight percent based on the weight of the silicone pressure sensitive adhesive of a cohesive strengthening agent selected from the group consisting of nonionic surfactants, fatty acid esters of glycerol, and solid particulate materials, said soild particulate materials being selected from the group consisting of metallic salts of fatty acids, metallic salts of phosphoric acid, metallic salts of carbonic acid, polysaccharides, carboxypolymethylene, polyvinyl pyrrolidone, polyvinylalcohol, and amorphous precipitated silicas having a surface area of between about 10 and 200 $m^2/g$, the adhesive matrix including compositions selected from the group consisting of drugs, co-solvents, enhancers, excipients, and mixtures thereof where the silicone pressure sensitive adhesive is compatible with said drugs, co-solvents, enhancers and excipients; and
    (c) a release liner contacted on the matrix.

2. The matrix transdermal drug delivery device of claim 1, wherein the drugs are selected from the group consisting of cardiovascular agents, antiarrthymic agents, antianginal agents, antibiotics, antifungals, antimicrobials, antihypertensives, analgesics, local anesthetics, contraceptives, hormonal supplements, anti-smoking agents, appetite suppressants, hypnotics, anxiolytics, and mixtures thereof.

3. The matrix transdermal drug delivery device of claim 1, wherein the co-solvents, enhancers and excipients are selected from the group consisting of fatty acid esters, polyols, surfactants, terpenes, glycerol esters, polyethylene glycol esters, amides, sulfoxides, lactams, nonionic surfactants, sorbitan esters, and mixtures thereof.

4. The matrix transdermal drug delivery device of claim 1, wherein the matrix is between about 1 and about 15 mils thick.

5. A matrix transdermal drug delivery device, comprising:
  (a) a backing substrate;
  (b) a matrix which is a polymer atop at least portions of said backing substrate, the matrix containing compositions selected from the group consisting of drugs, excipients, enhancers, co-solvents and mixtures thereof, where the matix is compatible with said compositions;
  (c) a silicone, creep resistant, pressure sensitive adhesive disposed in a layer atop at least portions of the polymer matrix; the silicone pressure sensitive adhesive comprising (i) from about 60 to about 30 parts by weight of a silicone fluid; (ii) from about 40 to about 70 parts by weight of a silicate resin, wherein the total parts of the silicone fluid and silicate resin equal 100 parts; and (iii) from about 1.0 to about 20.0 weight percent based on the weight of the silicone pressure sensitive adhesive of a cohesive strengthening agent selected from the group consisting of nonionic surfactants, fatty acid esters of glycerol, and solid particulate materials, said solid particulate materials being selected from the group consisting of metallic salts of fatty acids, metallic salts of phosphoric acid, metallic salts of carbonic acid, polysaccharides, carboxypolymethylene, polyvinyl pyrrolidone, polyvinylalcohol, and amorphous precipitated silicates having a surface area of between about 10 and 200 m$^2$/g, and
  (d) a release liner attached to the silicone pressure sensitive adhesive.

6. The matrix transdermal drug delivery device of claim 5, wherein the drugs are selected from the group consisting of cardiovascular agents, antiarrthymic agents, antianginal agents, antibiotics, antifungals, antimicrobials, antihypertensives, analgesics, local anesthetics, contraceptives, hormonal supplements, anti-smoking agents, appetite suppressants, hypnotics, anxiolytics, and mixtures thereof.

7. The matrix transdermal drug delivery device of claim 5, wherein the co-solvents, enhancers and excipients are selected from the group consisting of fatty acid esters, polyols, surfactants, terpenes, glycerol esters, polyethylene glycol esters, amides, sulfoxides, lactams, surfactants, sorbitan esters, and mixtures thereof.

8. The matrix transdermal drug delivery device of claim 5, wherein the matrix is between about 1 and about 15 mils thick.

9. A reservoir transdermal drug delivery device, comprising:
  (a) a backing substrate;
  (b) a reservoir attached to at least portions of the backing substrate, said reservoir containing compositions selected from the group consisting of drugs, co-solvents, enhancers, excipients, and mixtures thereof;
  (c) a silicone pressure sensitive adhesive attached to the reservoir and to portions of the backing substrate not covered by the reservoir; the silicone pressure sensitive adhesive comprising (i) from about 60 to about 30 parts by weight of a silicone fluid; (ii) from about 40 to about 70 parts by weight of a silicate resin, wherein the total parts of the silicone fluid and silicate resin equal 100 parts; and (iii) from about 1.0 to about 20.0 weight percent based on the weight of the silicone pressure sensitive adhesive of a cohesive strengthening agent selected from the group consisting of nonionic surfactants, fatty acid esters of glycerol, and solid particulate materials, said solid particulate materials being selected from the group consisting of metallic salts of fatty acids, metallic salts of phosphoric acid, metallic salts of carbonic acid, polysaccharides, carboxypolymethylene, polyvinyl pyrrolidone, polyvinylalcohol, and amorphous precipitated silicas having a surface area of between about 10 and 200 m$^2$/g, and
  (d) a release liner attached to the silicone pressure sensitive adhesive.

10. The reservoir transdermal drug delivery device of claim 9, wherein the drugs are selected from the group consisting of cardiovascular agents, antiarrthymic agents, antianginal agents, antibiotics, antifungals, antimicrobials, antihypertensives, analgesics, local anesthetics, contraceptives, hormonal supplements, anti-smoking agents, appetite suppressants, hypnotics, anxiolytics and mixtures thereof.

11. The reservoir-type transdermal drug delivery device of claim 9, wherein the co-solvents, enhancers and excipients are selected from the group consisting of fatty acid esters, polyols, surfactants, terpenes, glycerol esters, polyethylene glycol esters, amides, sulfoxides, lactams, nonionic surfactants, sorbitan esters and mixtures thereof.

12. The reservoir transdermal drug delivery device of claim 9, wherein the silicone pressure sensitive adhesive is between about 1 and about 15 mils thick.

13. The reservoir transdermal drug delivery device of claim 10, further comprising a rate controlling membrane, said rate controlling membrane being positioned over said reservoir and sealing the reservoir between the backing substrate and the rate controlling membrane.

14. The matrix transdermal drug delivery device of claim 1, wherein the cohesive strengthening agent is selected from the group consisting of calcium stearate, magnesium stearate, sodium stearate, calcium carbonate, calcium phosphate, polyvinylalcohol, xanthan gum, and silicas.

15. The matrix transdermal drug delivery device of claim 1, wherein the cohesive strengthening agent has a particle size ranging from about 0.018 to about 100 microns.

16. The matrix transdermal druge delivery device of claim 1, wherein the cohesive strengthening agent is present in an amount of between about 5 and about 15 weight percent.

17. The matrix transdermal drug delivery device of claim 5, wherein the cohesive strengthening agent is selected from the group consisting of calcium stearate, magnesium stearate, sodium stearate, calcium carbonate, calcium phosphate, polyvinylalcohol, xanthan gum, and silicas.

18. The matrix transdermal drug delivery device of claim 5, wherein the cohesive strengthening agent has a particle size ranging from about 0.018 to about 100 microns.

19. The matrix transdermal drug delivery device of claim 5, wherein the cohesive strengthening agent is present in an amount of between about 5 and about 15 weight percent.

20. The reservoir transdermal drug delivery device of claim 9, wherein the cohesive strengthening agent is selected from the group consisting of calcium stearate, magnesium stearate, sodium stearate, calcium carbonate, calcium phosphate, polyvinylalcohol, xanthan gum, and silicas.

21. The reservoir transdermal drug delivery device of claim 9, wherein the cohesive strengthening agent has a particle size ranging from about 0.018 to about 100 microns.

22. The reservoir transdermal drug delivery device of claim 9, wherein the cohesive strengthening agent is present in an amount of between about 5 and about 15 weight percent.

* * * * *